United States Patent [19]

Ljungquist

[11] Patent Number: 5,772,630
[45] Date of Patent: Jun. 30, 1998

[54] INJECTION CARTRIDGES

[75] Inventor: Olle Ljungquist, Täby, Sweden

[73] Assignee: Pharmacia AB, Stockholm, Sweden

[21] Appl. No.: 619,634

[22] PCT Filed: Sep. 16, 1994

[86] PCT No.: PCT/SE94/00864

§ 371 Date: Mar. 27, 1996

§ 102(e) Date: Mar. 27, 1996

[87] PCT Pub. No.: WO95/09020

PCT Pub. Date: Apr. 6, 1995

[30] Foreign Application Priority Data

Sep. 29, 1993 [SE] Sweden .................................. 9303178

[51] Int. Cl.$^6$ .................................................... A61M 37/00
[52] U.S. Cl. .............................. 604/90; 604/89; 604/191
[58] Field of Search .............................. 604/90, 89, 181, 604/191

[56] References Cited

U.S. PATENT DOCUMENTS

| | | |
|---|---|---|
| 4,439,184 | 3/1984 | Wheeler . |
| 5,298,024 | 3/1994 | Richmond .................................. 604/90 |
| 5,476,449 | 12/1995 | Richmond .................................. 604/87 |
| 5,549,569 | 8/1996 | Lynn et al. .............................. 604/191 |

FOREIGN PATENT DOCUMENTS

94/01150  1/1994  WIPO .

*Primary Examiner*—Michael Buiz
*Assistant Examiner*—N. Kent Gring
*Attorney, Agent, or Firm*—Pepper Hamilton LLP

[57] ABSTRACT

An injection cartridge is disclosed which has provision for the after injection of a rinsing solution to wash off the medicament that is first injected. The novel cartridge has a forward compartment and a rearward compartment, each having a piston disposed rearwardly thereof. A by-pass conduit is provided at the forward end of the cartridge which is longer than the thickness of the forwardmost piston. A medicament is positioned in the forward compartment and a rinsing solution is positioned in the rearward compartment. Moving the rearward piston forward forces the rinsing solution against the forward piston which in turn forces the medicament forward and expels it from the forward compartment. After the forward piston has reached its forward stop, the forward by-pass becomes open to the rearward compartment and continued forward movement of the rearward piston causes the rinsing solution to be forced through the forward by-pass and out the outlet end of the cartridge. This arrangement is particularly useful where the outlet is a tube and an injection needle or cannula.

37 Claims, 4 Drawing Sheets

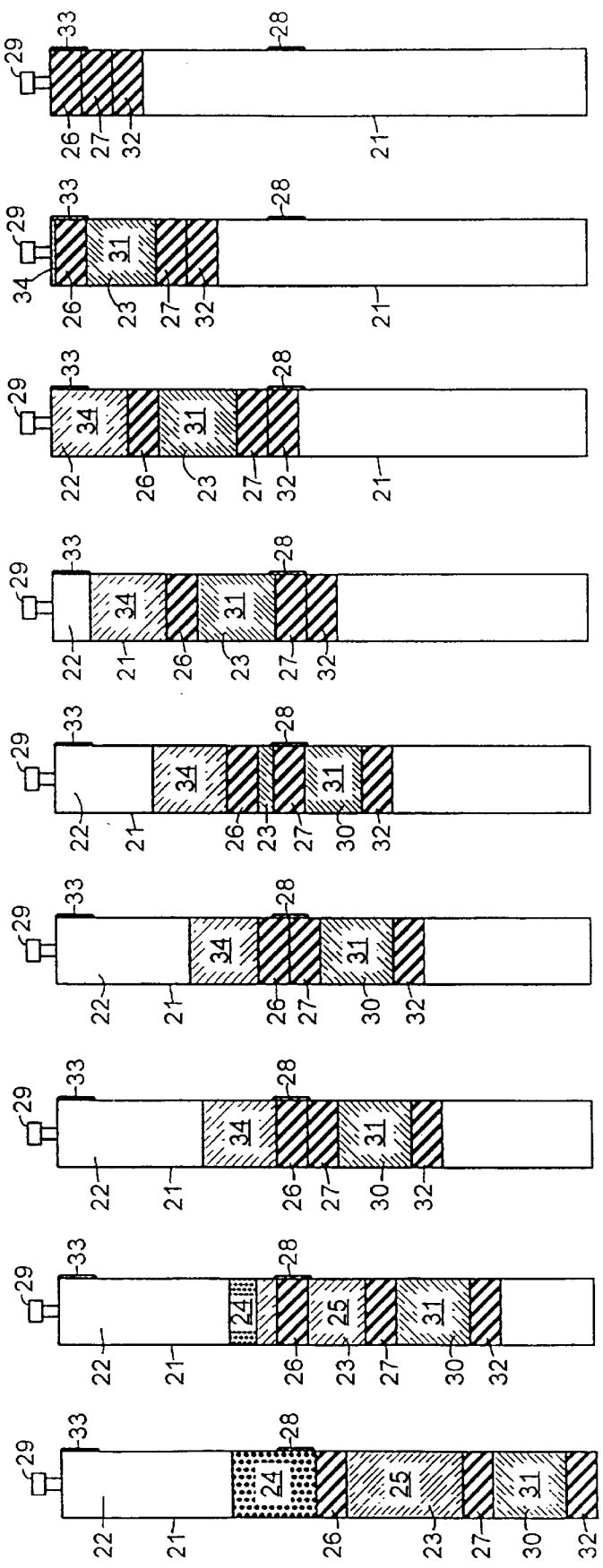

INJECTION CARTRIDGES

The present invention refers to an improvement in injection cartridges for administering parenteral injections or infusions. More particularly, the invention refers to an improvement in such injection cartridges which makes possible a better utilization of the injectable preparation used. The invention also refers to a method for administering a liquid preparation with the use of an injection cartridge of the invention. Furthermore, the invention also refers to the use of an injection cartridge of the invention for intravenous injection.

Injection cartridges have found a wide use for administering injectable pharmaceutical preparations by means of parenteral injection or infusion. Such cartridges have a number of important advantages, such as their ease of handling and the lessened risk of microbial contamination. An injection cartridge generally comprises a tubular barrel, which contains a liquid injectable preparation. At its front end, the barrel is sealed by a closure, which may be pierced by an outlet conduit, such as an injection needle or cannula or a tube for infusion. At its rear end, the cartridge is closed by a piston, which may be moved forward to expel the injectable preparation from the cartridge through the outlet conduit. This type of injection cartridge is known as a single-chamber injection cartridge.

Dual-chamber injection cartridges are also well-known. Such cartridges are intended to be used for injectable preparations which are not stable in their ready-to-use state, and their space between the front closure and the rear piston is divided into two chambers, which are separated by a movable wall. The front chamber usually contains a solid component of the injectable preparation, and the rear chamber contains a liquid component of said preparation. At a predetermined position in the cartridge, there is arranged a liquid bypass connection in the interior wall of the cartridge, such that the liquid component may bypass the movable separating wall and flow into the front chamber to be mixed with the solid component. When a forwardly directed pressure is applied to the rear piston, this pressure will be translated through the liquid to urge the movable wall forward, and when this wall is at the position of the bypass connection, the liquid will flow around said wall to be mixed with the component in the front chamber. In this way, the two components may be mixed with each other just before the injection is to be administered, and there will be no time for degradation of the ready-mixed preparation. When all the liquid has been transferred to the front chamber, the rear piston will abut the movable wall, and on further movement forward they will act as a single piston for expelling the mixed preparation from the cartridge.

U.S. Pat. No. 4,439,184 discloses a two-dose syringe with a dual chamber, intended to provide two separate bodies of fluid in a sequence. In the prefarred embodiment, a lubricating antiseptic and a lubricating anesthetic are used for preparing the urethra for catheterization. The lubricating properties of both the antiseptic and the anesthetic make it easier for the catheter to be slid into the urethra.

The design and function of single-chamber and dual-chamber injection cartridges is well-known to those skilled in the art, and need not be described here in closer detail.

When the administration of a liquid preparation from the injection cartridge has been finished and the rear piston is in its foremost position, there still exists a certain dead volume in front of the piston in the front end part and the outlet of the cartridge. This dead volume can be considerable, especially when a tube of some length is arranged between the outlet and the needle or cannula. This is a disadvantage, as it means that a certain amount of the pharmaceutical preparation will not be utilized by the patient. The disadvantage is aggravated when very expensive pharmaceutical preparations are used, such as growth hormones and certain peptides.

Various ways have been tried to eliminate this disadvantage. One way has been to draw some blood back into the cartridge after the finished injection and then inject it back into the patient, so that the outlet is rinsed in this way. This practice, however, is not to be recommended, as there is a risk that the components of the blood, which are very sensitive to surfaces, will be destroyed or coagulate to form clots. Another way has been to remove the syringe containing the pharmaceutical agent and replace it with a syringe containing a rinsing liquid, such as physiological saline solution, to finish the injection. This is complicated and time-consuming, and increases the risk of spillage and contamination.

The above-mentioned disadvantage is eliminated by the improvement of the present invention. According to the invention, there is provided an improvement in injection cartridges wherein a liquid preparation is expelled from the cartridge through an outlet conduit arranged at the front end of said cartridge by means of the displacement of a piston arranged in said cartridge. What characterizes the invention is that behind a front piston for the expulsion of the preparation is arranged a supplementary chamber in said cartridge and containing a rinsing liquid, said supplementary chamber being sealed at its rear end by a rear movable piston, and that a liquid bypass connection is arranged at the front end of the cartridge, such that when the front piston is in its foremost position, the rinsing liquid may be caused to flow around said front piston and out through said outlet conduit while rinsing said conduit.

In a preferred embodiment of the invention, the injection cartridge is a dual-chamber cartridge wherein a front chamber contains a solid component of the preparation, and a rear chamber contains a liquid component of the preparation, said chambers being separated by a displaceable separating wall, and wherein a rear liquid bypass connection is arranged in the interior wall of the cartridge, such that the liquid component may be caused to bypass said separating wall and flow into the front chamber to be mixed with the solid component, said rear chamber being closed at its rear end by said front piston, and the supplementary chamber for the rinsing liquid is arranged in said cartridge behind said front piston and is closed at its rear end by the rear movable piston. In In a still further preferred embodiment, the volume of the rinsing liquid is at least twice the combined volume of any space in the cartridge in front of the front piston in its foremost position and the space in the outlet conduit.

The invention will now be described in more detail, reference being made to the accompanying drawing:

FIG. 7 shows a dual-chamber injection cartridge according to the invention before it has been readied for injection.

FIG. 8 shows a dual-chamber injection cartridge according to the invention while it is being readied for injection.

FIG. 9 shows a dual-chamber injection cartridge according to the invention after the injectable preparation has been reconstituted in the front chamber.

FIG. 10 shows a dual-chamber injection cartridge according to the invention during an intermediate stage after the reconstitution of the injectable preparation.

FIG. 11 shows a dual-chamber injection cartridge according to the invention where the rinsing solution is flowing into the chamber formed behind the movable wall.

FIG. 12 shows a dual-chamber injection cartridge according to the invention which has been readied for the administration of an injection.

FIG. 13 shows a dual-chamber injection cartridge according to the invention during the administration of an injection.

FIG. 14 shows a dual-chamber injection cartridge according to the invention after finished administration of an injection, but before the rinsing step.

FIG. 15 shows a dual-chamber injection cartridge according to the invention after the rinsing step has been finished.

Figure 1:
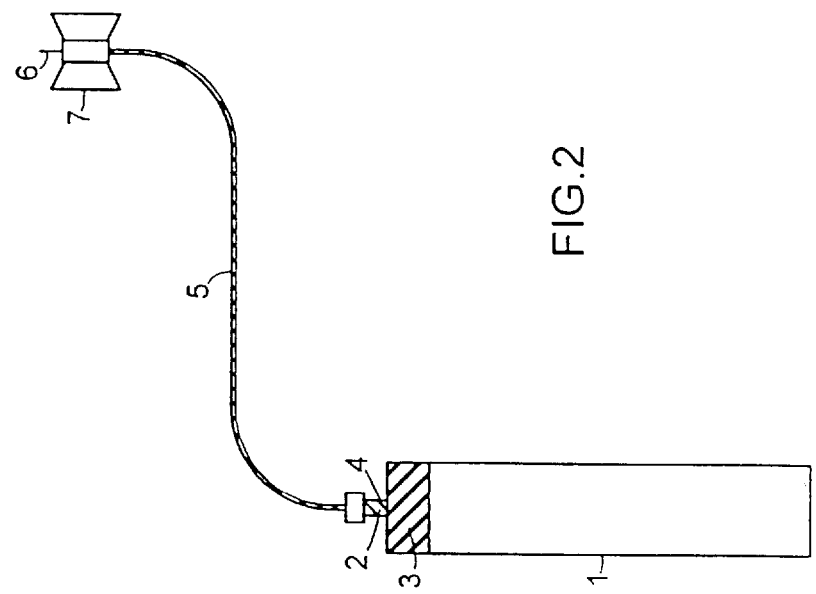
FIG. 1 shows an injection cartridge according to the prior art before an injection is administered.

In the figures of the drawing, the injection cartridges are only shown schematically, as the design in detail of these cartridges is well-known to those skilled in the art. Like parts in the figures have the same reference numbers. It is also to be noted that the drawing only serves to illustrate the invention, and not to limit its scope in any way.

FIG. 1 schematically shows a single-chamber injection cartridge according to the prior art where an administration of an injectable preparation has just started. The Injection cartridge comprises a barrel 1, which is filled with a liquid injectable preparation 2. The chamber filled with this preparation 2 is sealed at its rear end by a piston 3. At its front end, the cartridge is provided with an outlet conduit 4, and in the embodiment shown, this conduit is connected to a tube 5, which in its turn is connected to an injection needle or cannula 6. Near the injection needle 6 is arranged a device 7, such as a surgical adhesive tape, for securing the needle 6 to the patient's skin. The administration of the injectable preparation 2 has just started, as is shown by the somewhat advanced position of the piston 3 and the drop of preparation shown at 8.

Figure 2:
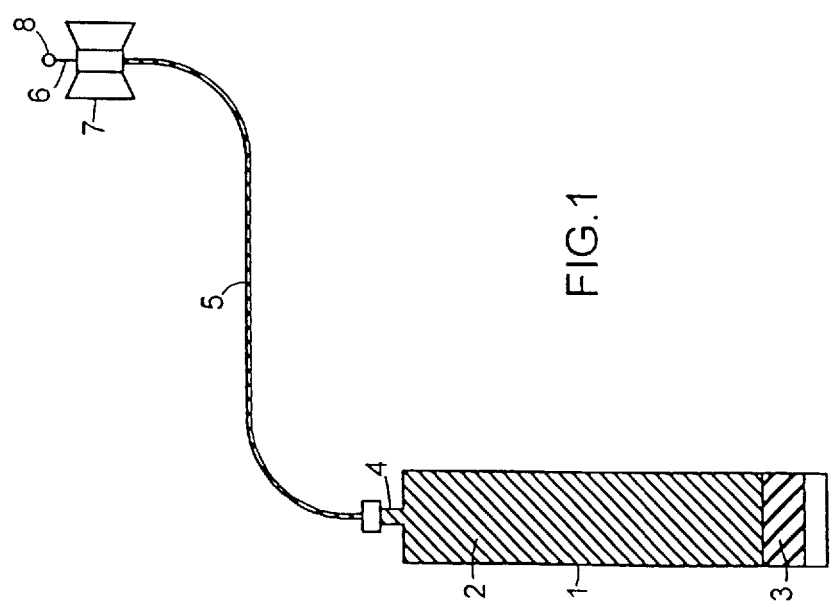
FIG. 2 shows an injection cartridge according to the prior art after an injection has been administered.

FIG. 2 shows the prior art cartridge after the administration has been finished. The piston 3 is at its foremost position in the barrel 1 and substantially all of the injectable preparation 2 has been expelled from the cartridge. However, there is a certain amount of this preparation 2 remaining in the dead volume provided by the outlet conduit 4 and the tube 5. This amount cannot be utilized by the patient and will usually be wasted. Such a waste may be quite important from an economical point of view when very expensive injectable preparations are administered, such as growth hormones and certain peptides. As has been stated in the foregoing, there has up to now not been provided any suitable way of remedying this inconvenience.

Figure 3:
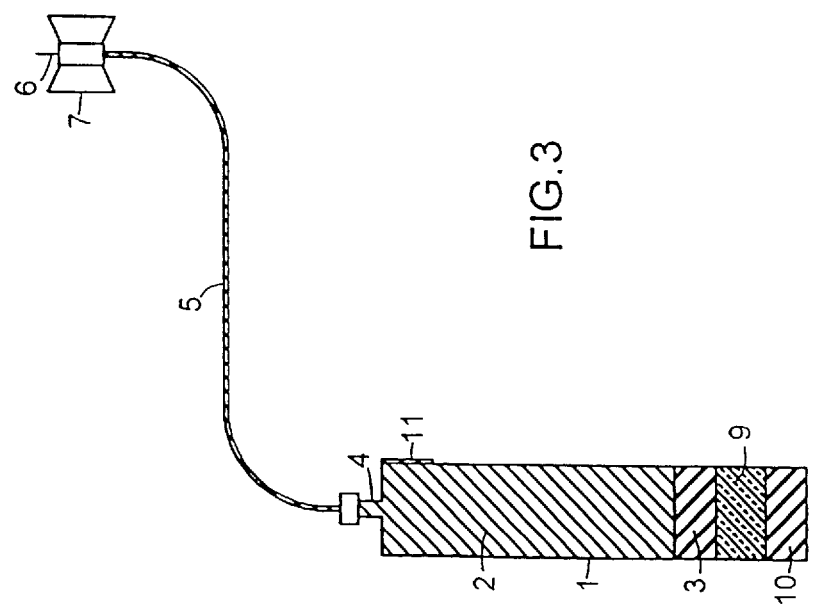
FIG. 3 shows an injection cartridge according to the invention before an injection is administered.

FIG. 3 shows a single-chamber injection cartridge according to the present invention before an administration has started. As previously shown, the injection cartridge comprises a barrel 1 which contains a liquid injectable preparation 2, and the chamber containing this preparation is sealed at its rear end by a front piston 3. At its front end, the cartridge is also provided with an outlet conduit 4, which is connected to an injection needle or cannula 6 via a tube 5.

However, the barrel 1 is extended rearward and comprises a supplementary chamber which is filled with a rinsing liquid 9 and is sealed at its rear end by a rear piston 10. Furthermore, there is arranged a liquid bypass connection 11 near the front end of the cartridge. This bypass connection may be arranged in any of several ways well-known to those skilled in the art. For instance, it may consist of a channel arranged in the interior wall of the barrel 1 or of some other modification of the interior wall of the barrel. The liquid bypass connection may also be of the so-called "negative" type, wherein the interior of the cartridge is provided with a constriction such that the piston 3 will be deformed when it is in this position. The basic object to be fulfilled by the liquid bypass connection is that the piston 3 should not seal completely against said interior wall when it is in the position of said bypass connection.

Figure 4:
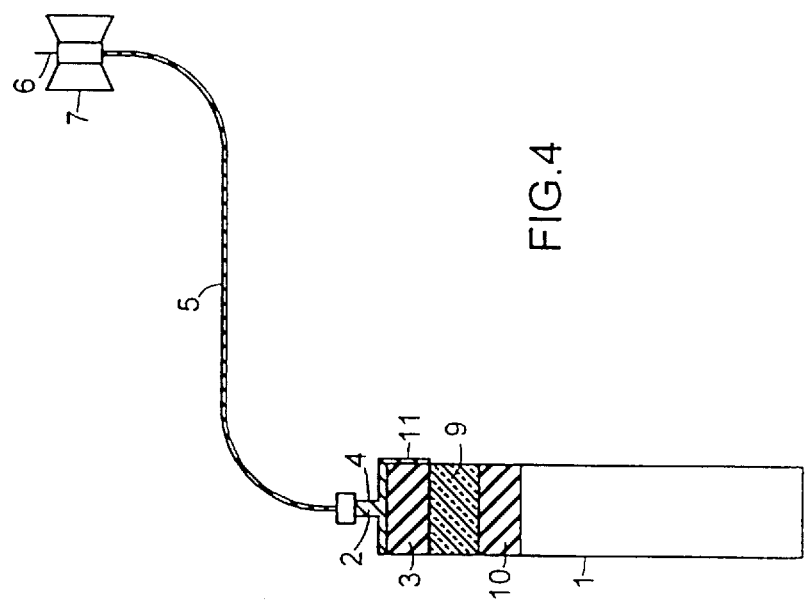
FIG. 4 shows an injection cartridge according to the invention after an injection has been administered, but before the rinsing step has started.

FIG. 4 shows the single-chamber injection cartridge according to the invention after essentially all of the injectable preparation has been expelled from the cartridge. The front piston 3 is in its foremost position in the barrel 1, but there is still a small amount of the injectable preparation 2 remaining in the dead volume afforded by the outlet conduit 4, the tube 5 and the liquid bypass connection 11. At its foremost position, the, front piston 3 is situated at the liquid bypass connection 11 in such a way that a liquid flow path is afforded from the chamber behind the front piston 3 around said front piston and into the dead space in front of it.

Figure 5:
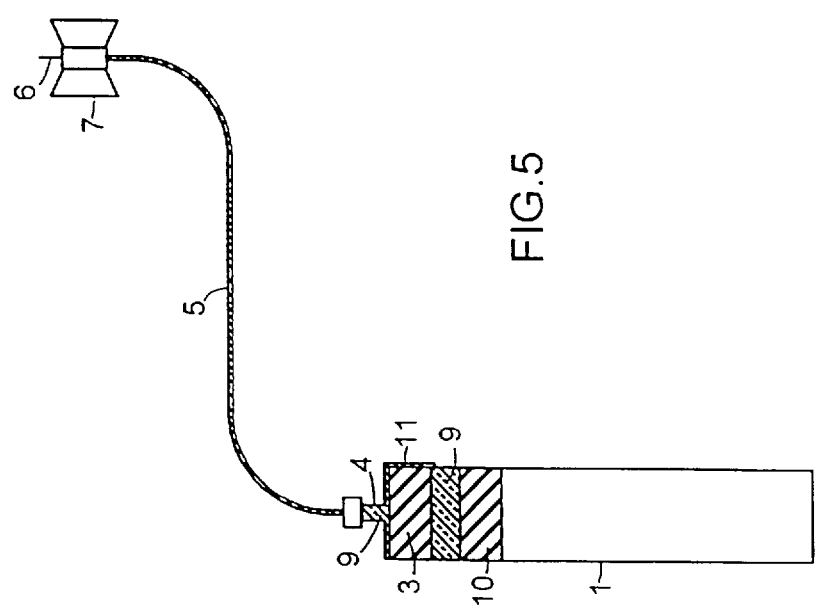
FIG. 5 shows an injection cartridge according to the invention during the rinsing step.

FIG. 5 shows the single-chamber injection cartridge according to the invention after the rinsing step has started. The rear piston 10 has now been moved forward such that the rinsing liquid 9 has been made to flow through the liquid bypass connection 11 around the piston 3 and out into the dead volume afforded by the outlet conduit 4 and the tube 5, thereby expelling the injectable preparation previously present in this dead volume through the injection needle or cannula 6 into the patient.

Figure 6:
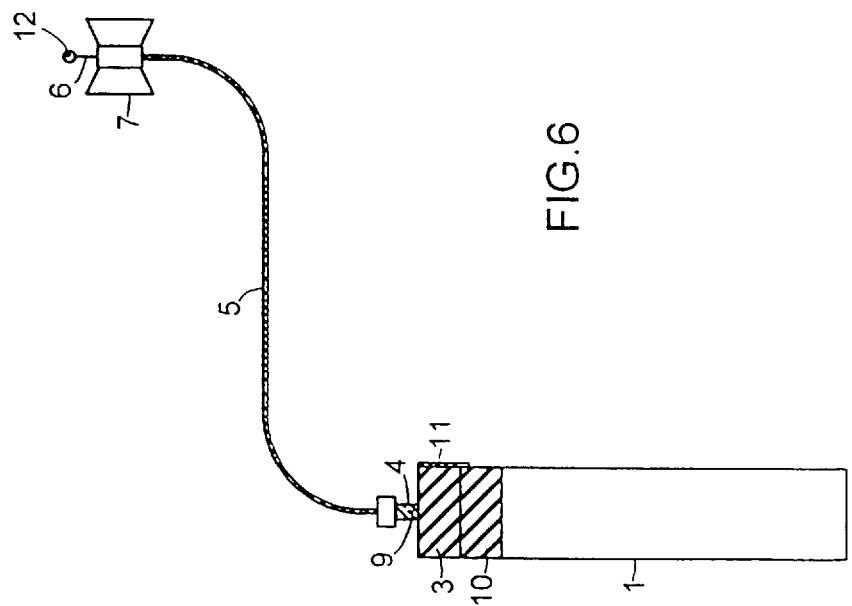
FIG. 6 shows an injection cartridge according to the invention after the rinsing step is finished.

FIG. 6 shows the single-chamber injection cartridge according to the invention after all of the rinsing liquid has been expelled from the cartridge. The rear piston is now abutting the front piston 3, and the outlet conduit 4 and the tube 5 contain substantially only the rinsing liquid 9. Substantially all of the injectable preparation has now been injected through the injection needle or cannula 6, together with a main portion of the rinsing liquid, as is illustrated by the drop 12.

FIG. 7 shows a dual-chamber injection cartridge according to the invention. This cartridge comprises a tubular barrel 21, which is divided into a front chamber 22 and a rear chamber 23. The front chamber 22 contains the solid component 24 of an injectable preparation, and the rear chamber 23 contains the liquid component 25 of said injectable preparation. The front chamber 22 and the rear chamber 23 are separated by a sealing movable wall 26, and the rear chamber 23 is sealed at its rear end by the front piston 27. In the interior wall of the cartridge barrel 1 is arranged a liquid bypass connection 28. At the front end of the cartridge is arranged an outlet conduit 29 through which the injectable preparation may be expelled. The outlet conduit 29 is connected to an injection needle or cannula directly or via a tube, as shown in FIGS. I to 6. For clarity, these details are not shown in FIGS. 7 to 15.

The above-mentioned features of the dual-chamber injection cartridge of the invention are well-known from conventional prior art injection cartridges of the dual-chamber type.

The barrel 21 of the injection cartridge of the present invention extends behind the front piston 27 to form a supplementary chamber 30. This chamber 30 is filled-with a rinsing liquid 31 and is sealed at its rear end by a rear piston 32. Furthermore, a-liquid bypass connection 33 is arranged at the front end of the cartridge.

FIG. 8 shows the dual-chamber injection cartridge according to the invention after the rear piston 32 has been moved forward so far that the movable wall 26 is situated at the position of the liquid bypass connection 28 and a portion of the liquid component 25 has been made to flow over from the rear chamber 23 into the front chamber 22. Thus, the liquid component 25 is mixed with the solid component 24 to dissolve it or suspend it, forming the ready-to-use injectable preparation. The rinsing liquid 31 is still enclosed in the supplementary chamber 30 between the front piston 27 and the rear piston 32.

FIG. 9 shows the dual-chamber injection cartridge according to the invention after all of the liquid component has been urged over into the front chamber 22, to form the injec-table preparation 34 together with the solid component. The front piston 27 now abuts the movable wall 26, and the rear chamber temporarily does not exist. Through the movement of the rear piston 32 and the front piston 27, the supplementary chamber 30 with the rinsing liquid 31 has been moved forward, but is otherwise unaffected.

FIG. 10 shows the dual-chamber injection cartridge according to the invention after the rear piston 32 and consequently also the front piston 27 and the movable wall 26 have been moved further forward so far that said front piston 27 and movable wall 26 cover the liquid bypass connection 28. This bypass connection 28 is therefore inactive at this stage.

FIG. 11 shows the dual-chamber injection cartridge according to the invention after the rear piston has been moved further forward such that the front piston 27 is at the position of the liquid bypass connection 28. On further forward movement of the rear piston 32, the rinsing liquid 31 will start to flow around the front piston 27 and out into the space between the movable wall 26 and the front piston 27, thus recreating the rear chamber 23 and filling it with the rinsing liquid 31. The injectable preparation 34 in the front chamber is also moved forward, but is otherwise unaffected.

FIG. 12 shows the dual-chamber injection cartridge according to the invention after all of the rinsing liquid 31 has been urged over into the rear chamber 23. The rear piston 32 now abuts the front piston 27, and these two pistons now act as one single piston, while the former supplementary chamber 30 has now disappeared.

FIG. 13 shows the dual-chamber injection cartridge according to the invention after the front and rear pistons 27 and 32, and consequently also the movable wall 26, have been advanced so far forward that the front chamber 22 is now filled completely with the injectable preparation 34. This preparation can now be expelled from the cartridge through the outlet conduit 29 to start the administration to a patient. The liquid bypass connection is now inactive.

FIG. 14 shows the dual-chamber injection cartridge according to the invention after substantially all of the injectable preparation 34 has been expelled from the cartridge and administered to the patient. There is now a certain portion of said preparation remaining in the dead volume in the carridge in front of the movable wall 26 and in the outlet conduit 29 and a possible tube (not shown) to an injection needle or cannula (not shown).

When the movable wall 34 is in its foremost position, it is situated at the position of the front liquid bypass connection 33, which thereby becomes active and allows the rinsing liquid 31 to bypass said movable wall 34 and flow out in the dead volume in front of it. On further movement forward of the combined front and rear pistons 27 and 32, the rinsing liquid 31 will be urged through the liquid bypass connection 33 and expelled from the cartridge through the outlet conduit 29, to displace the remainder of the injectable preparation and expel it through the injection needle or cannula into the patient. Thus it will be seen that all of the injectable preparation will be administered to the patient, and there will be no waste.

FIG. 15 shows the dual-chamber injection cartridge according to the invention after all of the rinsing liquid has been expelled through the outlet conduit 29. The movable wall 26, the front piston 27 and the rear piston 32 now abut each other, and the liquid bypass connection 33 is inactive. The administration from the cartridge is now finished.

The administration of the injectable preparation and subsequent rinsing from a single-chamber injection cartridge, as well as the readying, administration and rinsing from a dual-chamber injection cartridge according to the invention is carried out by urging the piston 3 (FIGS. 3–6) or the rear piston 32 (FIGS. 7–15) forward by means of a piston rod. Such a piston rod may be moved forward by simple axial forward pressure, by a screw mechanism, or by a combination of the two. Various arrangement for achieving this are well-known to those skilled in the art, and need not be described here in closer detail.

The function of a dual-chamber injection cartridge according to the invention is as follows:

The injection cartridge is usually supplied to the user in the state as shown and described in FIG. 7. When the cartridge is to be readied for an administration, the user applies forward pressure on the rear piston 32 by means of a suitable piston rod (not shown). This pressure is translated through the substantially incompressible liquids 25 and 31 in the rear chamber 23 and the rear end chamber 30, respectively, such that the movable wall 26 and the front piston 27 are also urged forward. When the movable wall 26 has reached the position of the liquid bypass connection 28, this connection becomes active to allow a flow of the liquid component 25 around said movable wall 26 to become mixed with the solid component in the front chamber 22. The solid component 24 will then become dissolved or dispersed in the liquid component 25 to form the injectable preparation 34.

When the front piston 26 has been moved so far forward that all of the liquid component has been urged over into the front chamber 22, the front piston 26 will abut the movable wall 26. Further forward movement of the rear piston 32 will move the front piston 27 and the movable wall 26 forward together until said front piston 27 is at the position of the liquid bypass connection 28. This by pass connection 28 will now become active again such that the rinsing liquid may flow around the front piston 27. On further forward movement of the rear piston 3 2, the front piston 27 will remain stationary while the movable movable wall 26 will be urged forward and the rinsing liquid 31 will bypass the front piston 27 to fill the space created between said movable wall 26 and said front piston 27. When all of the rinsing liquid has been urged over into said space, the rear piston 32 will abut the front piston 27, and on further movement forward, these two pistons will act as a single piston.

When the two pistons 27 and 32 are further moved forward, the movable wall 26 will serve to expel the mixed injectable preparation 34 through the out let conduit 29, which has been connected to an injection needle or cannula, optionally via a tube. The injection needle or cannula is now connected to a patient an d the administration of said injectable preparation can now take place.

After finished administration, the movable wall 26 is at its foremost position in the cartridge barrel 21, and substantially all of the injectable preparation has been expelled from the cartridge. However, there remains a certain portion of the preparation in the dead volume consisting of the space in front of the movable wall 26, the outlet conduit 29 and the attached tube and injection needle. This portion will not be utilized by the patient if no special measures are taken according to the invention.

At its foremost position, the movable wall 26 is positioned at the front liquid bypass connection 33 in such a way that a flow path for the rinsing liquid is provided around said movable wall. Further pressure forward on the combined pistons 27 and 32 will now make the rinsing liquid 31 flow around the movable wall 26 and out into the outlet conduit 29 and the attached tube and needle or cannula. In doing so, the rinsing liquid 31 will displace the remaninder of the injectable preparation such that it is adminstered to the patient and the outlet conduit 29 and the tube are rinsed. Thus there will be no waste of the injectable preparation. When all of the rinsing liquid 31 has been expelled from the cartridge, the administration is finished.

The injection cartridge is usually arranged in a holder device to facilitate its use in the administering of an injection. Such holder devices are also conventional and well-known to those skilled in the art. The injection cartridge according to the invention does not require any substantial design changes of the known holder devices. Small alterations may be necessary to accommodate the front bypass connection and the greater length of the cartridge, but these are within the competence of a person skilled in this art. The materials used for the manufacture of injection cartridges of the invention are the same as those used for conventional injection cartridges, such as glass and various plastic and rubber materials. Thus, with a cartridge comprising a front chamber containing a liquidpreparation and a supplementary chamber containing the rinsing liquid, the front piston may be made of any resilient material, preferably rubber. However, when the the cartridge of the invention is used for lyophilization to obtain a solid component, the movable wall between the front chamber and the rear chamber should be made of a resilient material with a low permeability for water.vapour A suitable material is butyl rubber, preferably a halo-butyl rubber, such as chlorobutyl or bromobutyl rubber. Also, when the cartridge of the invention is used for lyophilization, the barrel of the cartridge should be made of a rigid material, to better withstand the low pressure and themperature used in the lyophilization process. A suitable material is glass.

It is important that the volume of the rinsing liquid is sufficient to effect a thorough rinsing of the dead volume and displace the remaining injectable preparation to inject it into the patient. It has been found that the volume of the rinsing liquid should be at least twice, and preferably at least three times the combined volume of the space in the injection cartridge in front of the front piston or the movable wall in its foremost position and the space in the outlet conduit to the injection needle or cannula. This gives a thorough rinsing effect.

The injection cartridge of the invention can be used with any of those injectable preparations that have been found to be suitable in conventional injection cartridges. As examples can be mentioned therapeutic proteins and peptides. However, the advantages offered by the invention become more pronounced when very expensive preparations are administered, suitably those produced by recombinant DNA technology. Typical examples are growth hormones, certain peptides, anticancer drugs, vaccines, interleukines, monoclonal antibodies, tissue plasmin activator (tPA), erythropoietin (EPO), urokinase, streptokinase, low molecular weight heparins and human proteins. More particularly, the human proteins are factor VI H, factor IX or antithrombin m I, produced by recombinant DNA technology. For such preparations, the avoidance of waste is of a great economic importance.

Suitable liquid injectable preparations include solutions containing human proteins, such as factor VIII, factor IX and antithrombin I fI, with at least one stabilizing agent, such as a surfactant. Suitable solid components of an injectable preparation include lyophilized human proteins, preferably factor VIII produced by recombinant DNA technology.

The injection cartridge of the present invention is suitably used for parenteral ad ministration, such as subcutaneous, intramuscular or intravenous injection, preferably then intravenous injection. More preferably, the injection cartridge of the present invention is used for rinsing the outlet conduit connected to a tube and an injection needle or cannula from esentially all of the injectable preparation. The injection cartridge of the present invention is suitably used for the administering of any human protein, preferably then a lyophilized protein.

The method for administering a liquid preparation from an injection syringe of the present invention is suitably used in parenteral administration, such as subcutaneous, intramuscular or intravenous injection, preferably then intravenous injection. More preferably, the method for administering a liquid preparation is used for rinsing the outlet conduit connected to a tube and an injection needle or cannula from essentially all of the injectable preparation. The method for administering a liquid preparation from an injection cartridge of the present invention is suitably used for the administering of any human protein, preferably then a lyophilized protein.

The rinsing liquid may be any liquid which is compatible with the injectable preparation and which does not cause any detrimental effects when administered to a patient. A number of such liquids are known to those skilled in the art, and as an example may be mentioned physiological saline solution.

In the foregoing specification, the invention has been described with reference to embodiments shown in the drawings. However, to a person skilled in the art, it is clear that these embodiments are only examples and do not serve to limit the scope of the invention in any way. Other variations and modifications of the invention are possible within the scope of the appended claims.

I claim:

1. Injection cartridge, adapted to expel a liquid medicament preparation from a main chamber through an outlet conduit, tube and injection needle or cannula arranged at the front end of said cartridge by the displacement of a front piston arranged rearward of said main chamber in said cartridge, characterized in that behind said front piston, for the expulsion of said medicament preparation is arrange a supplementary chamber in said cartridge, said supplementary chamber being adapted to contain a rinsing liquid, which is different from said medicament preparation, said supplementary chamber being sealed at its rear end by means of a longitudinally moveable rear piston, and that at the front end of said cartridge is arranged a liquid by-pass conduit in a wall of said cartridge and of a length greater than a thickness of said front piston such that when said front piston is in its foremost position, said rinsing liquid is adapted to flow through said liquid by-pass conduit in said wall around said front piston and out through the outlet conduit tube and injection needle or cannula, for rinsing said outlet conduit, tube and injection needle or cannula.

2. Injection cartridge according to claim 1, characterized in that the volume of said rinsing liquid is at least twice the combined volume of any space in the cartridge in front of the front piston and the space in said outlet conduit.

3. Injection cartridge according to claim 1, characterized in that the liquid bypass conduit is arranged in the exterior wall of the cartridge.

4. Injection cartridge according to claim 1, characterized in that the liquid bypass conduit is arranged as a channel in the interior wall of the cartridge, or as some other modification of said interior wall.

5. Injection cartridge according to claim 1, characterized in that the movable front piston between the front chamber and the rear chamber consists of butyl rubber.

6. Injection cartridge according to claim 1, characterized in that housing of said cartridge comprises glass.

7. Injection cartridge according to claim 1, characterized in that the medicament preparation contains a human protein.

8. Injection cartridge, adapted to expel a liquid medicament preparation through an outlet conduit arranged at the front end of said cartridge by the displacement of a piston arranged in said cartridge, characterized in that said cartridge comprises:
- a forward chamber adapted to house said medicament preparation;
- a front piston, for the expulsion of said medicament preparation, arranged rearward of said forward chamber;
- a supplementary chamber in said cartridge, containing a rinsing liquid, rearward of said front piston;
- a rear moveable piston disposed rearwardly of said supplemental chamber, and
- a liquid bypass conduit disposed at the front end of said cartridge such that when the front piston is in its foremost position, said rinsing liquid is adapted to flow around said front piston, through said bypass conduit, and out through the outlet conduit while rinsing the conduit;
- wherein said forward chamber of said injection cartridge is a dual chamber comprising a front chamber containing a solid component of said injectable preparation, and a rear chamber containing a liquid component of said preparation,
- wherein said front and rear chambers are separated by a moveable wall, and
- a rear liquid bypass conduit arranged in the interior wall of said cartridge, such that the liquid component is adapted to flow around said moveable wall into admixture with said solid component,
- wherein the rear chamber is sealed at its rear end by said front piston, and
- wherein said supplementary chamber for rinsing liquid is arranged in said cartridge behind said front piston and is sealed at its rear end by said rear moveable piston.

9. Injection cartridge according to claim 8, characterized in that the volume of said rinsing liquid is at least twice the combined volume of any space in the cartridge in front of the front piston and the space in said outlet conduit.

10. Injection cartridge according to claim 8, characterized in that the liquid bypass conduit at the front end of the cartridge is arranged in the exterior wall.

11. Injection cartridge according to claim 8, characterized in that the liquid bypass conduit is arranged as a channel in the interior wall of the cartridge, or as some other modification of said interior wall.

12. Injection cartridge according to claim 8, characterized in that the injectable preparation is expelled through a tube and an injection needle or cannula.

13. Injection cartridge according to claim 8, characterized in that the solid component is a lyophilized human protein.

14. Injection cartridge according to claim 8, characterized in that the movable wall between the front chamber an the rear chamber consists of butyl rubber.

15. Injection cartridge according to claim 8, characterized in that the external portion of said cartridge comprises glass.

16. The use of an injection cartridge according to claim 8 for intravenous injection.

17. The use of an injection cartridge according to claim 16, for intravenous injection through the outlet conduit connected to a tube and an injection needle or cannula.

18. The use according to claim 16, for intravenous injection of a human protein.

19. A method of administering a liquid medicament preparation to a patient from a front chamber of an injection cartridge comprising:
- expelling said preparation from said front chamber through an outlet conduit arranged at the front end of said cartridge by means of forward movement of a front piston;
- forwardly pushing a rear moveable piston, which together with said front piston and a wall of said cartridge defines and seals a supplementary chamber disposed rearward of said front piston, containing a rinsing liquid, whereby moving said rinsing liquid, said front piston and said medicament preparation, respectively, forward; and
- flowing said rinsing liquid through a liquid bypass conduit disposed in a wall of said cartridge, around said front piston when it is in its foremost position and out through the outlet conduit;
- whereby rinsing residues of said medicament preparation from said outlet conduit.

20. A method according to claim 19, characterized in that the injectable preparation is expelled through a tube and an injection needle or cannula.

21. A method according to claim 19, characterized in that the volume of said rinsing liquid is at least twice the combined volume of any space in the cartridge in front of the front piston and the space in said outlet conduit.

22. A method according to claim 19, characterized in that the solid component is a lyophilized human protein.

23. A method according to claim 19, characterized in that the movable wall between the front chamber an the rear chamber consists of butyl rubber.

24. A method according to claim 19, characterized in that the external portion of said cartridge comprises glass.

25. The use of an injection cartridge to claim 1 for intravenous injection.

26. The use according to claim 25, for intravenous injection of a human protein.

27. An injection cartridge comprising:
- a housing having an outlet assembly at a forward end thereof for expelling at least a portion of the contents of the housing;
- wherein said outlet comprises an outlet conduit, a tube and an injection needle or a cannula;
- wherein said housing is internally divided into at least one forward chamber and at least one rearward chamber said rearward chamber being adapted to contain a rinsing liquid that is different in composition from the contents of said forward chamber, which chambers are disposed in tandem within said housing;

at least one forwardly and at least one rearwardly disposed transversely positioned piston, with said forward piston disposed between said chambers and said rearward piston disposed rearward of said rearward chamber;

a forward bypass conduit longitudinally disposed in a wall of said housing and at a forward end of said housing of a length which is greater than the thickness of said forward piston;

wherein said forward bypass conduit is so positioned as to provide a longitudinal passageway through said wall around the forward piston when the forward piston is at a forward-most position;

wherein a forward end of said forward bypass conduit communicates directly with said outlet assembly; and means to longitudinally move said pistons whereby:
  initially progressing the contents of said forward chamber through said outlet assembly; and
  thereafter, progressing said rinsing solution through said bypass conduit and outlet assembly in a quantity sufficient to wash at least a substantial portion of any contents of said forward chamber from said outlet assembly.

28. An injection cartridge as claimed in claim 27 wherein the volume of the rearward chamber is at least twice the volume of the forward chamber.

29. An injection cartridge as claimed in claim 27 wherein the liquid bypass conduit is disposed in an exterior wall of said cartridge.

30. An injection cartridge as claimed in claim 27 wherein the liquid bypass conduit is disposed in or on an interior wall of said cartridge.

31. An injection cartridge as claimed in claim 27 wherein the contents of said front chamber are a medicament.

32. An injection cartridge comprising:

a housing having an outlet assembly at a forward end thereof for expelling at least a portion of the contents of the housing;

wherein said housing is internally divided into at least one rearward chamber adapted to contain a rinsing liquid, and at least one forward chamber adapted to contain a material that is different in composition from the contents of said rearward chamber, which chambers are disposed at least partially in tandem within said housing;

wherein said forward chamber is divided into at least one forward sub-chamber and at least one rearward sub-chamber;

a forward sub-piston disposed between said forward and said rearward sub-chambers;

a rearward sub-piston disposed between said rearward sub-chamber and said rearward chamber;

a rearward piston disposed rearwardly of said rearward chamber;

a longitudinal intermediate bypass conduit disposed such that when said chambers are all filled and said rearward piston is moved forward, one end of said intermediate bypass conduit is adapted to communicate with said forward sub-chamber and another end thereof is adapted to communicate with said rearward sub-chamber; and a longitudinally disposed forward bypass conduit adapted to communicate between said outlet assembly and said rearward sub-chamber when said forward and rearward sub-pistons are both at their forwardmost stop positions.

33. An injection cartridge as claimed in claim 32 wherein said intermediate bypass conduit has a length which is not longer than the longitudinal dimension of said rearward sub-chamber.

34. An injection cartridge as claimed in claim 32 wherein said contents of said forward chamber comprise a medicament.

35. An injection cartridge as claimed in claim 34 wherein said medicament comprises at least two components, one adapted to be disposed in said forward sub-chamber and the other disposed in said rearward sub-chamber; wherein said medicament is constituted when said components are mixed together.

36. A method of administering an injectable composition to a patient which comprises:

disposing said injectable composition in a forward chamber of a multi-chambered an injection cartridge;

disposing a longitudinally acting forward piston immediately rearward of said forward chamber;

disposing a rinsing composition, which is different from said injectable composition, in a rearward chamber of said injection cartridge;

disposing a longitudinally acting rearward piston immediately rearward of said rearward chamber;

applying forwardly acting longitudinal pressure on said rearward piston sufficient to move said rinsing solution, said forward piston and said injectable composition, respectively, forward in tandem and to expel said injectable composition from said forward chamber and out of said cartridge through an outlet assembly, and to longitudinally move said forward piston to a forward stopped position without expelling said rinsing composition; and applying additional forwardly acting longitudinal pressure on said rearward piston sufficient to cause said rinsing solution to proceed through a forward bypass conduit disposed in a wall of said cartridge around said forward piston and out through said outlet assembly, whereby rinsing all of the injectable composition out of said outlet assembly.

37. The method claimed in claim 36 further comprising:

dividing said forward chamber into at least two sub-chambers, a forward sub-chamber and a rearward sub-chamber;

disposing said forward piston immediately rearward of said forward sub-chamber, thereby defining said forward sub-chamber forward of said forward piston;

disposing an intermediate piston immediately rearward of said rearward sub-chamber, thereby defining said rearward sub-chamber between said forward piston and said intermediate piston;

applying forwardly acting longitudinal pressure on said rearward piston sufficient to cause a first composition disposed in said rearward sub-chamber to proceed through an intermediate bypass conduit and into admixture with a second composition disposed in said forward sub-chamber;

mixing said first and second compositions in said forward sub-chamber to form said injectable composition while bringing a forward end of said intermediate piston into a proximity relationship to a rearward end of said forward piston;

applying further forwardly acting pressure on said rearward piston sufficient to force said rinsing composition through said intermediate by-pass conduit into said rearward sub-chamber, thereby forwardly moving said rearward piston into a position proximate to the rearward end of said intermediate piston, and thereby moving said forward sub-chamber to a position proximate to said outlet assembly;

expelling said injectable composition through said outlet assembly by further forward movement of said rearward piston and moving said forward piston to a position proximate to said outlet assembly; and further moving said rearward piston forward thereby forcing said rinsing solution through said forward by-pass conduit around said forward piston, into a rinsing relationship with elements of said outlet assembly, and out of said outlet.

* * * * *